(12) United States Patent
Nayak et al.

(10) Patent No.: US 11,412,948 B2
(45) Date of Patent: Aug. 16, 2022

(54) METHOD FOR IMPROVED DYNAMIC CONTRAST ENHANCED IMAGING USING TRACER-KINETIC MODELS AS CONSTRAINTS

(71) Applicant: UNIVERSITY OF SOUTHERN CALIFORNIA, Los Angeles, CA (US)

(72) Inventors: Krishna Shrinivas Nayak, Long Beach, CA (US); Yi Guo, Los Angeles, CA (US); Robert Marc Lebel, Calgary AB (CA); Yinghua Zhu, San Jose, CA (US); Sajan Goud Lingala, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 1158 days.

(21) Appl. No.: 15/595,156

(22) Filed: May 15, 2017

(65) Prior Publication Data

US 2017/0325709 A1 Nov. 16, 2017

Related U.S. Application Data

(60) Provisional application No. 62/336,033, filed on May 13, 2016.

(51) Int. Cl.
| | |
|---|---|
| *A61B 5/055* | (2006.01) |
| *G01R 33/56* | (2006.01) |
| *A61B 5/00* | (2006.01) |
| *G01R 33/563* | (2006.01) |
| *G01R 33/561* | (2006.01) |

(52) U.S. Cl.
CPC ............ *A61B 5/055* (2013.01); *A61B 5/0042* (2013.01); *A61B 5/7257* (2013.01); *G01R 33/5601* (2013.01); *G01R 33/56366* (2013.01); *G01R 33/5611* (2013.01)

(58) Field of Classification Search
None
See application file for complete search history.

(56) References Cited

PUBLICATIONS

Aharon, M. et al., "K-SVD: An Algorithm for Designing Overcomplete Dictionaries for Sparse Representation," IEEE Transactions on Signal Processing, v. 54, n. 11, 2006, pp. 4311-4322.
(Continued)

*Primary Examiner* — Jonathan Cwern
(74) *Attorney, Agent, or Firm* — Brooks Kushman P.C.

(57) ABSTRACT

Tracer kinetic models are utilized as temporal constraints for highly under-sampled reconstruction of DCE-MRI data. The method is flexible in handling any TK model, does not rely on tuning of regularization parameters, and in comparison to existing compressed sensing approaches, provides robust mapping of TK parameters at high under-sampling rates. In summary, the method greatly improves the robustness and ease-of-use while providing better quality of TK parameter maps than existing methods. In another embodiment, TK parameter maps are directly reconstructed from highly under-sampled DCE-MRI data. This method provides more accurate TK parameter values and higher under-sampling rates. It does not require tuning parameters and there are not additional intermediate steps. The proposed method greatly improves the robustness and ease-of-use while providing better quality of TK parameter maps than conventional indirect methods.

11 Claims, 13 Drawing Sheets

(56) References Cited

PUBLICATIONS

Fluckiger, J.U. et al., "Model-based Blind Estimation of Kinetic Parameters in DCE-MRI," Magn Reson Med 2009, 62(6), pp. 1477-1486.

Lebel, R.M. et al., "Highly Accelerated Dynamic Contrast Enhanced Imaging," Magnetic Resonance in Medicine, 71 (2014), pp. 635-644.

Lingala, S.G. et al., "Accelerated DCE MRI Using Constrained Reconstruction Based on Pharmaco-Kinetic Model Dictionaries," Proc. ISMRM, 2015, p. 1539.

Lingala, S.G. et al., "Accelerated Brain DCE-MRI Using Contrast Agent Kinetic Models as Temporal Constraints," ISMRM Workshop on Data Sampling and Image Reconstruction, 2016, 1 pg.

Parker, G.J.M. et al., "Tracer Kinetic Modelling for T1-Weighted DCE-MRI," Springer Berlin Heidelberg, 2005, pp. 81-93.

Parker, G.J.M. et al., "Experimentally-Derived Functional Form for a Population-Averaged High-Temporal-Resolution Arterial Input Function for Dynamic Contrast-Enhanced MRI," Magnetic Resonance in Medicine, 56 (2006) pp. 993-1000.

Pati, Y.C., "Orthogonal Matching Pursuit: Recursive Function Approximation with Applications to Wavelet Decomposition," Proc. of the 27th Annual Asilomar Conference on Signals Systems and Computers, 1993, pp. 1-5.

Patlak, C.S. et al., "Graphical Evaluation of Blood-to-Brain Transfer Constants from Multiple-Time Update Data," J. of Cerebral Blood Flow and Metabolism, 3, (1983), pp. 1-7.

Simonis, F. FJ. et al., "Improving the Arterial Input Function in Dynamic Contrast Enhanced MRI by Fitting the Signal in the Complex Plane," Magnetic Resonance in Medicine, 00:00-00 (2015), pp. 1-10.

Tofts, P.S. et al., "Estimating Kinetic Parameters from Dynamic Contrast-Enhanced T1-Weighted MRI of a Diffusable Tracer: Standardized Quantities and Symbols," J. of Magnetic Resonance Imaging, 10, 1999, pp. 223-232.

Winkelmann, S. et al., "An Optimal Radial Profile Order Based on the Golden Ratio for Time-Resolved MRI," IEEE Transactions on Medical Imaging, v. 26, n. 1, 2007, pp. 68-76.

Zhu, Y. et al., "Randomized Golden Ratio Sampling for Highly Accelerated Dynamic Imaging," Proc. Intl. Soc. Mag. Reson. Med. 22 (2014), p. 4365.

Zhu, Y. et al., "GOCART: GOlden-angle CArtesian Randomized Time-Resolved 3-D MRI," Magnetic Resonance Imaging, 34 (2016), pp. 940-950.

METHOD FOR IMPROVED DYNAMIC CONTRAST ENHANCED IMAGING USING TRACER-KINETIC MODELS AS CONSTRAINTS

CROSS-REFERENCE TO RELATED APPLICATIONS

This application claims the benefit of U.S. provisional application Ser. No. 62/336,033 filed May 13, 2016, the disclosure of which is hereby incorporated in its entirety by reference herein.

STATEMENT REGARDING FEDERALLY SPONSORED RESEARCH OR DEVELOPMENT

The invention was made with Government support under Contract No. UL1TR000130 awarded by the National Institutes of Health. The Government has certain rights to the invention.

TECHNICAL FIELD

In at least one embodiment, the present invention relates to methods for improving magnetic resonance imaging.

BACKGROUND

Dynamic Contrast Enhanced Magnetic Resonance Imaging (DCE-MRI) is a time resolved methodology of MRI, which involves intravenous administration of a paramagnetic contrast agent and continuous acquisition of images to track the passage of the contrast through a volume of interest. DCE-MRI is used most often to evaluate cancer (tumor vascularity), but can also be applied to other diseases.

Tracer-kinetic (TK) modeling of the enhancement kinetics of the contrast agent enables quantification of TK parameters such as $K^{trans}$: a volume transfer coefficient across the capillary endothelium, and fractional volumes such as $v_e$ (fractional volume of the extravascular extracellular space), and $v_p$ (fractional plasma volume). These parameters provide a means as functional biomarkers in diagnosis and treatment planning of cancer in several body parts including the brain, breast, liver, and prostate. In the brain, DCE-MRI characterizes the blood-brain barrier leakiness, which has important implications as a potential early biomarker in the evaluation of neuro-degenerative diseases such as Alzheimer's disease, multiple sclerosis, and vascular dementia.

DCE-MRI is a 4-dimensional (x, y, z, time) imaging task, and is challenged by slow MRI acquisition speed. Conventional DCE-MRI imaging schemes based on "Nyquist rate" sampling (or full sampling) face a challenging tradeoff amongst the achievable spatial resolution, temporal resolution, and volume coverage. Acceleration techniques based on parallel imaging, and compressed sensing have demonstrated potential to improve the imaging trade-offs in DCE-MRI. These methods perform "sub-Nyquist" sampling (or under-sampling) to improve spatial resolution, spatial coverage, and/or image quality. Image recovery from under-sampled measurements is an ill-posed problem. Various constrained image-reconstruction strategies have been proposed to make the problem well-posed. Existing methods rely on "sparsity" assumptions of DCE-MRI data in transform domains such as spatio-temporal wavelet transform, spatio-temporal finite-difference transform, temporal Fourier transform. The challenge with such "off-the-shelf" transforms is that often the assumptions being made by the transforms do not fit with the data, which limits the achievable undersampling rates. In addition, image reconstruction with these transforms involves tuning regularization parameters, which poses challenges on the practical utility of these methods. Data-derived transforms have recently been proposed. While these methods have advantages over off-the-shelf transforms in adapting the transform representations to the data, they are associated with even more complex image reconstruction, which are often non-convex and involve tuning of additional free parameters.

Accordingly, there is a need for improved methods implementing dynamic contrast enhanced magnetic resonance imaging.

SUMMARY

The present invention solves one or more problems of the prior art by providing in at least one embodiment, a method for improving dynamic contrast enhanced imaging. The method including a step of administering a magnetic resonance contrast agent to a subject and then collecting magnetic resonance imaging data from the subject. The magnetic resonance imaging data includes (k-t) space data that may be under-sampled or fully sampled. A TK model is selected to be applied to the magnetic resonance imaging data. Characteristically, the tracer kinetic model is defined by a plurality of tracer kinetic parameters. The TK model is applied to obtain TK parameter maps.

In a variation of the method set forth above, a direct reconstruction of TK parameter maps in dynamic contrast enhanced magnetic resonance imaging is provided. The knowledge of the full forward model of mapping the kinetic parameters to the k-t space dynamic contrast enhanced magnetic resonance imaging data is exploited in this variation. The forward model utilizes a magnetic resonance imaging analytical simulator and a tracer kinetic model. MRI receiver coil sensitivities and an arterial input function can also be used in the model. Dynamic anatomic images are estimated from estimated contrast agent concentration versus time data to form estimated dynamic anatomic images. Similarly, (k,t) space data is estimated by applying Fourier transform, receiver coil sensitivity and under-sampling pattern to the estimated dynamic anatomic images to form estimated (k,t) space data. The estimated (k,t)-space data is compared to measured fully sampled or under-sampled (k,t)-space data. The tracer kinetic parameter maps are iteratively refined to minimize errors between measured and propagated (k,t)-space data to obtain optimal estimates of the tracer kinetic parameter maps.

In another variation of the method set forth above, a dictionary-based reconstruction of dynamic contrast enhanced magnetic resonance images is provided. This variation further includes a step of generating a library of simulated concentration time profiles for a magnetic resonance contrast agent by applying a tracer kinetic model having a plurality of tracer kinetic parameters. A dictionary of temporal basis functions is created from the simulated library of concentration time profiles such that the dictionary spans the sub-space of potential concentration time profiles. Estimated concentration time profiles for dynamic contrast enhanced magnetic resonance imaging at each spatial position is determined by finding the estimated concentration time profile that has an optimal projection on the dictionary of temporal basis functions.

DETAILED DESCRIPTION

Figure 1A:
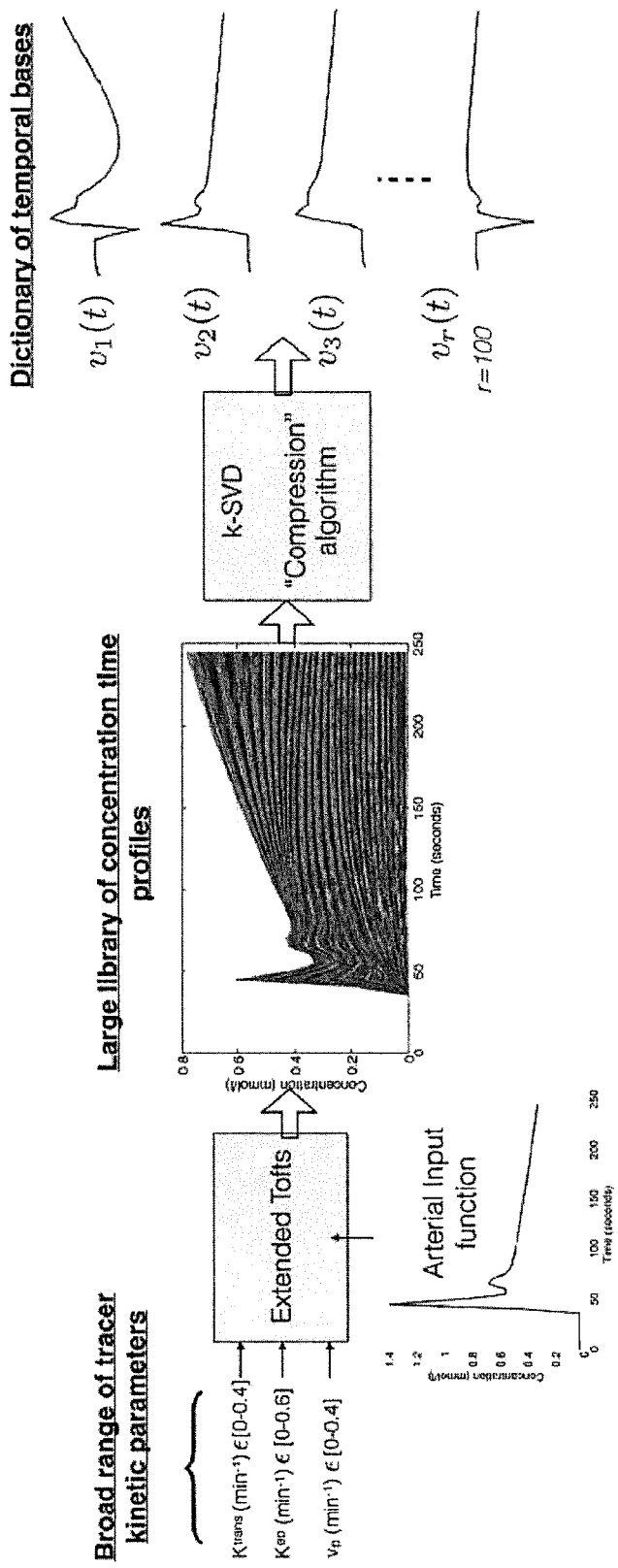
FIG. 1A. Construction of temporal basis functions (in a dictionary) from a specified tracer kinetic model. Basis functions derived from the extended Tofts-Kety (ETK) model are considered, and are used as temporal constraints to enable accelerated DCE-MRI.

Reference will now be made in detail to presently preferred compositions, embodiments and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

In an embodiment of the present invention, a method for improving dynamic contrast enhanced imaging is provided. The method includes a step of administering a magnetic resonance contrast agent to a subject and then collecting magnetic resonance imaging data from the subject. Typically, the magnetic resonance imaging data is collected from an imaging volume or imaging plane in the subject which can be presented as voxels or pixels. The magnetic resonance imaging data including (k,t)-space data with is essentially a spatial Fourier transform as a function of time. The reconstructed magnetic resonance imaging data is converted to contrast agent concentration time data. A tracer kinetic model is selected to be applied to the contrast agent concentration time data. Characteristically, the tracer kinetic model being defined by a plurality of tracer kinetic parameters. Typically, the method is applied to portions of the sample volume or area to provide estimated tracer kinetic parameters for each of these portions. This allows results to be presented for voxels or pixels. Examples of suitable contrast agents include gadolinium-containing compounds or formulations that are chelated for safety, such as gadoterate, gadodiamide, gadobenate, adopentetate, gadoteridol, gadofosveset, gadoversetamide, gadoxetate, gadobutrol, and the like and combinations thereof.

As set forth above present embodiment applies a tracer kinetic model. Examples of suitable tracer models are the Patlak and extended Tofts-Kety (ETK) model as set forth in P. S. Tofts, G. Brix, D. L. Buckley, J. L. Evelhoch, E. Henderson, M. V Knopp, H. B. Larsson, T. Y. Lee, N. a Mayr, G. J. Parker, R. E. Port, J. Taylor, and R. M. Weisskoff, "Estimating kinetic parameters from dynamic contrast-enhanced T(1)-weighted MRI of a diffusable tracer: standardized quantities and symbols," J. Magn. Reson. Imaging, vol. 10, no. 3, pp. 223-32, September 1999; and Parker, G. J. and Buckley, D. L., 2005. Tracer kinetic modelling for T1-weighted DCE-MRI. In *Dynamic contrast-enhanced magnetic resonance imaging in oncology* (pp. 81-92). Springer Berlin Heidelberg; the entire disclosures of these publications is hereby incorporated by reference. In general, the Patlak and ETK having kinetic parameters: $K^{trans}$ which is a transfer constant from blood plasma into extracellular extravascular space (EES) and $v_p$ which is fractional plasma volume. The ETK model also has kinetic parameters $K^{ep}$ which is a transfer constant from EES back to the blood plasma and $v_e$ which is a fractional EES volume ($v_e = K^{trans}/K^{ep}$). The concentration for the contrast agent in this model is calculated from:

$$\frac{dC_t}{dt} = K^{trans}(C_p - C_e) = K^{trans}(C_p - C_t/v_e)$$

where
$C_t$ is the equilibrium concentration of contrast agent in whole tissue;
$C_p$ is the equilibrium concentration of contrast agent in plasma;
$C_e$ is the equilibrium concentration of contrast agent in extracellular extravascular space. In the simple Toft model, the contrast concentration in whole tissue can be determined from:

$$C_t(t) = K^{trans} \int_0^t C_p(\tau) e^{-(K^{trans}/v_e)(t-\tau)}$$

When $v_p$ is considered such as in the ETK model, the contrast concentration in whole tissue can be determined from:

$$C_t(t) = v_p C_p(t) + K^{trans} \int_0^t C_p(\tau) e^{-(K^{trans}/v_e)(t-\tau)}$$

When the time dependent concentration is known, these equations can be inverted to estimate the kinetic parameters. Additional details for converting TK parameter (e.g., $K^{trans}$, $v_p$) maps to contrast concentration over time using the Patlak model is provided by P. S. Tofts, G. Brix, D. L. Buckley, J. L. Evelhoch, E. Henderson, M. V Knopp, H. B. Larsson, T. Y. Lee, N. a Mayr, G. J. Parker, R. E. Port, J. Taylor, and R. M. Weisskoff, "Estimating kinetic parameters from dynamic contrast-enhanced T(1)-weighted Mill of a diffusable tracer: standardized quantities and symbols," J. Magn. Reson. Imaging, vol. 10, no. 3, pp. 223-32, September 1999 and Patlak C. S., Blasberg R. G., Fenstermacher J. D. Graphical evaluation of blood-to-brain transfer constants from multiple-time uptake data. J. Cereb. Blood Flow Metab. 1983; 3:1-7; the entire disclosures of these publications is hereby incorporated by reference.

A variation that uses a direct reconstruction and a variation that uses a dictionary-based reconstruction of tracer-kinetic parameter maps in dynamic contrast enhanced magnetic resonance imaging are set forth below.

Figure 11:
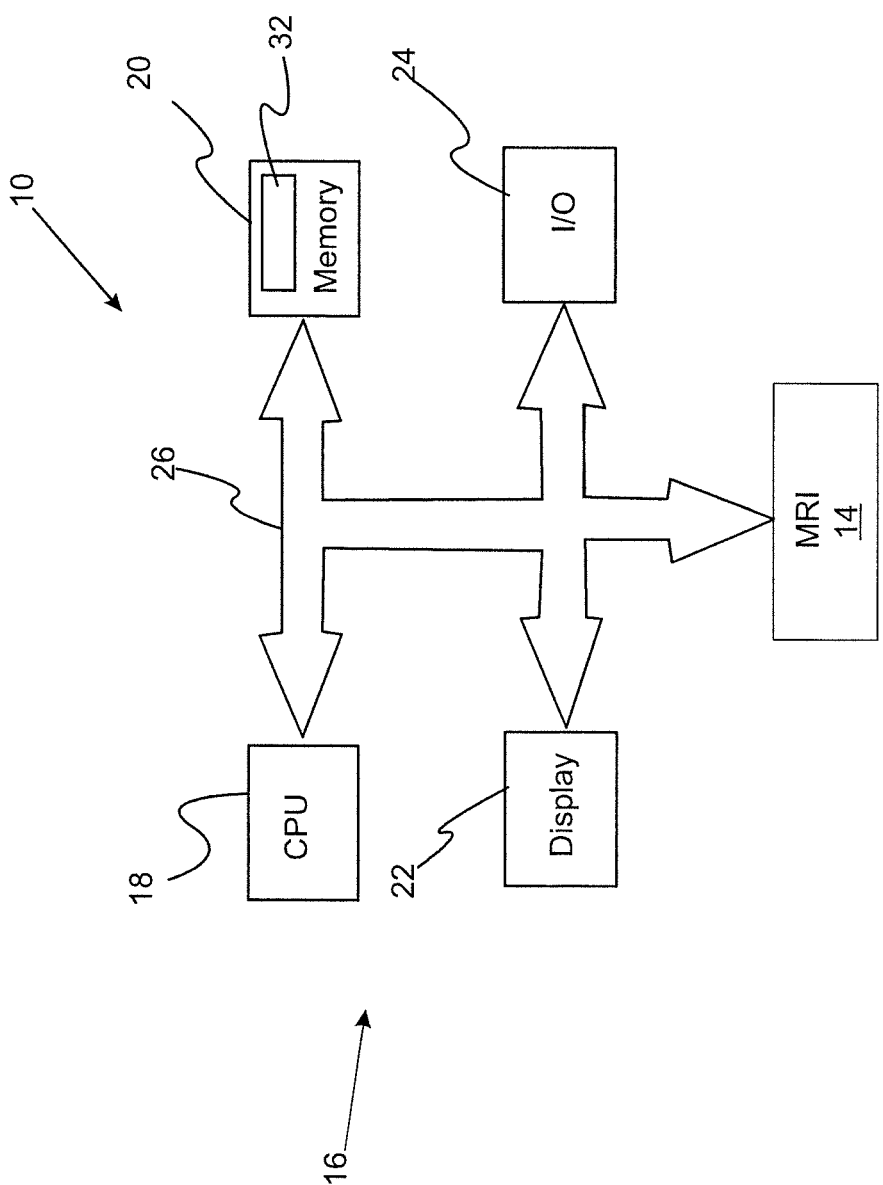
FIG. 11. Schematic of an image system that can implement the methods of the invention.

In another embodiment, a system for improving dynamic contrast enhanced imaging is provided. With reference to FIG. 11, imaging system 10 includes magnetic resonance imaging system 14, which can be a fast low angle shot magnetic resonance imaging system. Magnetic resonance imaging system 14 includes coils 15 from which the (k, t) space data is collected. Typically, system 14 implements a standard SPGR imaging sequence with a modifiable sampling trajectory. In a refinement, only phase encoding directions need to be reordered. Imaging system 10 also includes a programmable computer 16 for implement the step of applying the tracer kinetic model to the magnetic resonance imaging data. Computer system 16 includes central processing unit (CPU) 18, memory 20, displayer 22 and input/output interface 24 which communicate over buses 26. Computer system 16 communicates input devices 30 such as a keyboard and mouse via input/output interface 24. In one variation, memory 20 includes one or more of the following: random access memory (RAM), read only memory (ROM), CDROM, DVD, disk drive, tape drive. The method of the present variation is implemented by routine 32 that is stored in memory 20 and executed by the CPU 18

1. Method for Improved Dynamic Contrast Enhanced Imaging Using Tracer-Kinetic Models as Constraints In a variation, a method for improving dynamic contrast enhanced imaging is provided. The method includes a step of generating a library of simulated concentration time profiles for a magnetic resonance contrast agent by applying a tracer kinetic model having a plurality of tracer kinetic parameters. In general, the simulated concentration time profile is created over a parameter range of interest. For example, each simulated concentration time profile can be generated by stepping through a range for each tracer kinetic parameter at a predetermined time. A dictionary of temporal basis functions is created from the library of simulated concentration time profiles. For example, the library of simulated concentration time profiles can be compressed to a dictionary of temporal basis functions. In another refinement, the dictionary of temporal basis functions is the full library of simulated concentration time profiles or a subset thereof. The dictionary of temporal basis functions can be used analyze magnetic resonance data as follows. The magnetic resonance contrast agent is administered to a subject. Magnetic resonance imaging data is collected from an imaging volume or imaging plane in the subject over a predetermined period of time. Characteristically, the magnetic resonance imaging data can include or be fully sampled or under-sampled k-t space data. Estimated concentration time profiles $C_t(x,y,z,t)$ for the fully sampled or under-sampled k-t space data are determined by finding estimated concentration time profiles that has an optimal projection of projection on the dictionary of temporal basis functions. In this context, an optimal projection is defined by the user to meet predefined objectives. For example, the optimal projection might be the closest concentration time profile that falls within the subspace spanned by the dictionary. Alternatively, the optimal projection may also include Bayesian priors, or weights on the likelihood of each location within the subspace.

The present variation provides a novel model-based DCE-MRI constrained reconstruction technique, where contrast-agent TK models are used as temporal constraints (see for example, S. G. Lingala, Y. Guo, Y. Zhu, S. Barnes, R. M. Lebel, and K. S. Nayak, "Accelerated DCE MRI using constrained reconstruction based on pharmaco-kinetic model dictionaries," in *Proc ISMRM* 2015, 2015, p. 196 and S. G. Lingala, Y. Guo, Y. Zhu, N. Nallapareddy, R. M. Lebel, M. Law, and K. S. Nayak, "Accelerated brain DCE-MRI using Contrast Agent Kinetic Models as Temporal Constraints," in *ISMRM Workshop on Data Sampling and Image Reconstruction,* 2016; the entire disclosures of these publications is hereby incorporated by reference.)

The method of the present variation is unique because the constraints are designed based on contrast agent kinetic models that are already routinely used during post-processing of DCE-MRI data; they will therefore not introduce new assumptions with new potential artifacts. Furthermore, the method does not require tuning of any parameters, compared to current compressed sensing methods where a number of regularization parameters are required to be tuned. The proposed approach has flexibility in incorporating a wide variety of TK models, and is applicable to DCE-MRI of various organs and disease conditions, which would warrant use of different TK models. As an example, this invention describes the proposed approach using the extended-Tofts model in the application of brain tumor DCE-MRI, where robust mapping of TK-parameters up to under-sampling factors of 30 fold are demonstrated.

Model-based reconstruction has been previously proposed. While it is commonly used in dynamic positron emission tomography (PET) imaging, it has recently been adapted in MRI. In MRI, model-based approaches have been demonstrated in the applications of relaxometry, perfusion, and diffusion tensor imaging. Broadly, these methods can be classified into methods based on direct reconstruction of parameters from fully- or under-sampled data, or methods that use representations derived from parametric models as constraints in image reconstruction. This invention deals with a methodology in the second class of methods for DCE-MRI. The key advantages compared to existing methods are: a) flexibility to incorporate any tracer-kinetic model (including ones that are non-linear), b) exploitation of TK models as temporal constraints in the reconstruction, c) does not require selection of tuning parameters.

Technical Description

Figure 1B:
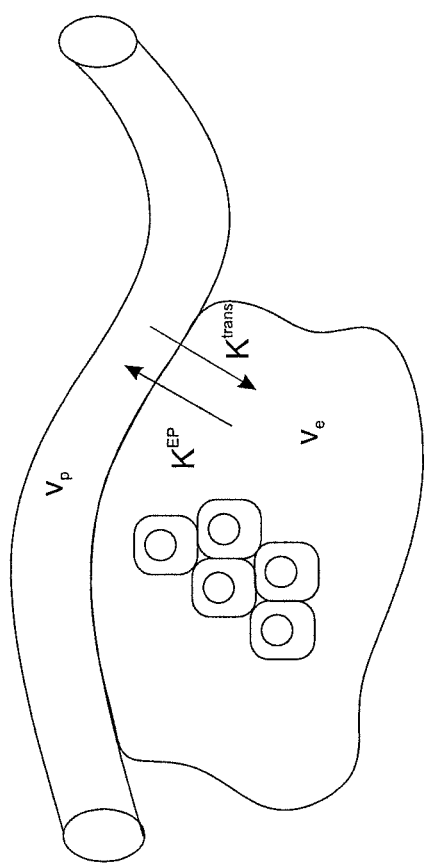
FIG. 1B. Schematic illustrating tracer kinetic parameters in the Tofts and ETK models.

The proposed approach has two steps: a) one-time construction of a dictionary of temporal basis functions from a TK model of choice, and b) constrained reconstruction of DCE-concentration time profiles with the TK-dictionary from under-sampled k-t data. The specifics of these two steps are now described:

Construction of Temporal Dictionary:

As depicted in FIG. 1, utilizing an appropriate TK model, a library of concentration vs. time profiles ($Z_{1 \times N}$) are simulated for a broad range of physiological kinetic parameters; 1 denotes the number of profiles in the library; and N denotes the number of time instances. For the ETK model (see, Parker, G. J. and Buckley, D. L., 2005. Tracer kinetic modelling for T1-weighted DCE-MRI. In *Dynamic contrast-enhanced magnetic resonance imaging in oncology* (pp. 81-92). Springer Berlin Heidelberg; the entire disclosure of which is hereby incorporated by reference) the following range was considered: $K^{trans}$=0-0.4 min$^{-1}$ in steps of 0.01 min$^{-1}$, $K^{ep}$=0-0.6 min$^{-1}$ in steps of 0.01 min$^{-1}$, $v_p$=0-40% in steps of 1%, using a population based arterial input function (Parker, G. J., Roberts, C., Macdonald, A., Buonaccorsi, G. A., Cheung, S., Buckley, D. L., Jackson, A., Watson, Y., Davies, K. and Jayson, G. C., 2006. Experimentally-derived functional form for a population-averaged high-temporal-resolution arterial input function for dynamic contrast-enhanced MRI. *Magnetic resonance in medicine*, 56(5), pp. 993-1000; the entire disclosure of which is hereby incorporated by reference) to yield a library of size 1×N=102541×50; A dictionary-learning algorithm (k-singular value decomposition (k-SVD) (see, Aharan et al. below) is then used to compress the large library to a smaller dictionary of temporal basis functions (denoted $V_{r \times N}$). A particularly useful dictionary-learning algorithm is set forth in Aharon, M., Elad, M. and Bruckstein, A., 2006. K-SVD: An Algorithm for Designing Overcomplete Dictionaries for Sparse Representation. *IEEE Transactions on signal processing*, 54(11), p. 4311; the entire disclosure of this publication is hereby incorporated by reference.

The concentration profiles in Z are modeled as a "k-sparse" linear combination of temporal basis functions in the dictionary wherein k number of basis functions are selected from the dictionary to model a concentration time profile of interest in Z. This means that the concentration time profile at each spatial position can be approximated using a linear combination of k temporal basis functions. The model represents the simulated concentration profiles in Z as a product of a sparse coefficient matrix (U) and the dictionary (V): $Z_{1 \times N} = U_{1 \times r} V_{r \times N}$; r denotes the number of bases in the dictionary chosen as r=100>N=50, but significantly less than 1. The rows of U are modeled to be sparse, meaning that there are only k non-zero entries (k<r) in every row ($u_i$) of U. The objective criterion of k-SVD can be mathematically expressed as:

$$\min_{U,V} \|Z - UV\|_2^2; \ s \cdot t \cdot \|u_i\| \le k; \quad (1)$$

wherein k is a sparsity parameter, and represents the number of non-zero entries in every row ($u_i$) of the matrix U. The sparsity parameter k is proposed to be tuned based on model-approximation errors, and noise sensitivity analysis described below, where the objective is to determine the smallest k for which the resulting k-sparse projected dictionary modeled profiles yield no parameter bias, and comparable variance, after e-Tofts modeling.

Figure 2:
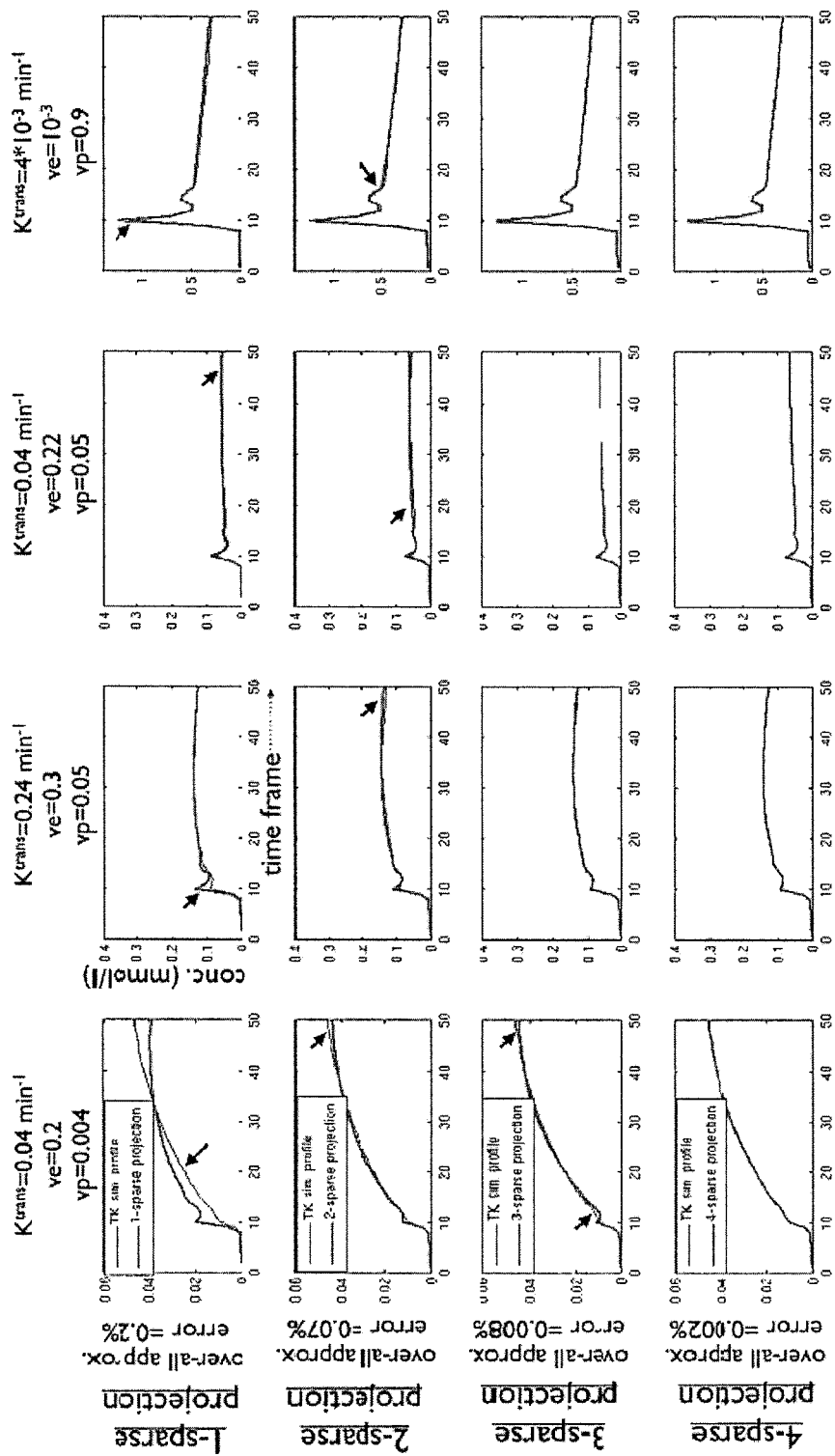
FIG. 2. Modeling of concentration time profiles generated from the ETK model (blue profiles) using dictionaries constructed from a dictionary compression technique, k-SVD, at different sparsity levels (k) (red profiles). While lower values of k introduces considerable model approximation error (see black arrows), a choice of k=4 is shown to mimic profiles produced from the ETK model within an overall approximation error of 0.002%.

Model-Approximation Error (Noise-Less Simulations):

In FIG. 2, we analyze the approximation error between the concentration time profiles generated from the ETK model, and the concentration time profiles synthesized by the learned dictionary at varied sparsity levels (k). While there exists model approximation errors of >0.05% for lower values of k (k<2), the overall approximation error is reduced to <0.01% at k>=3. It can also be noted that for curves generated with low Ktrans <0.1 min−1, k=4 is required for improving the approximation. In the specified range of TK parameters considered, we found that k=4 produced an over-all approximation error of at most 0.008%, and closely mimicked the ETK model.

Figure 3:
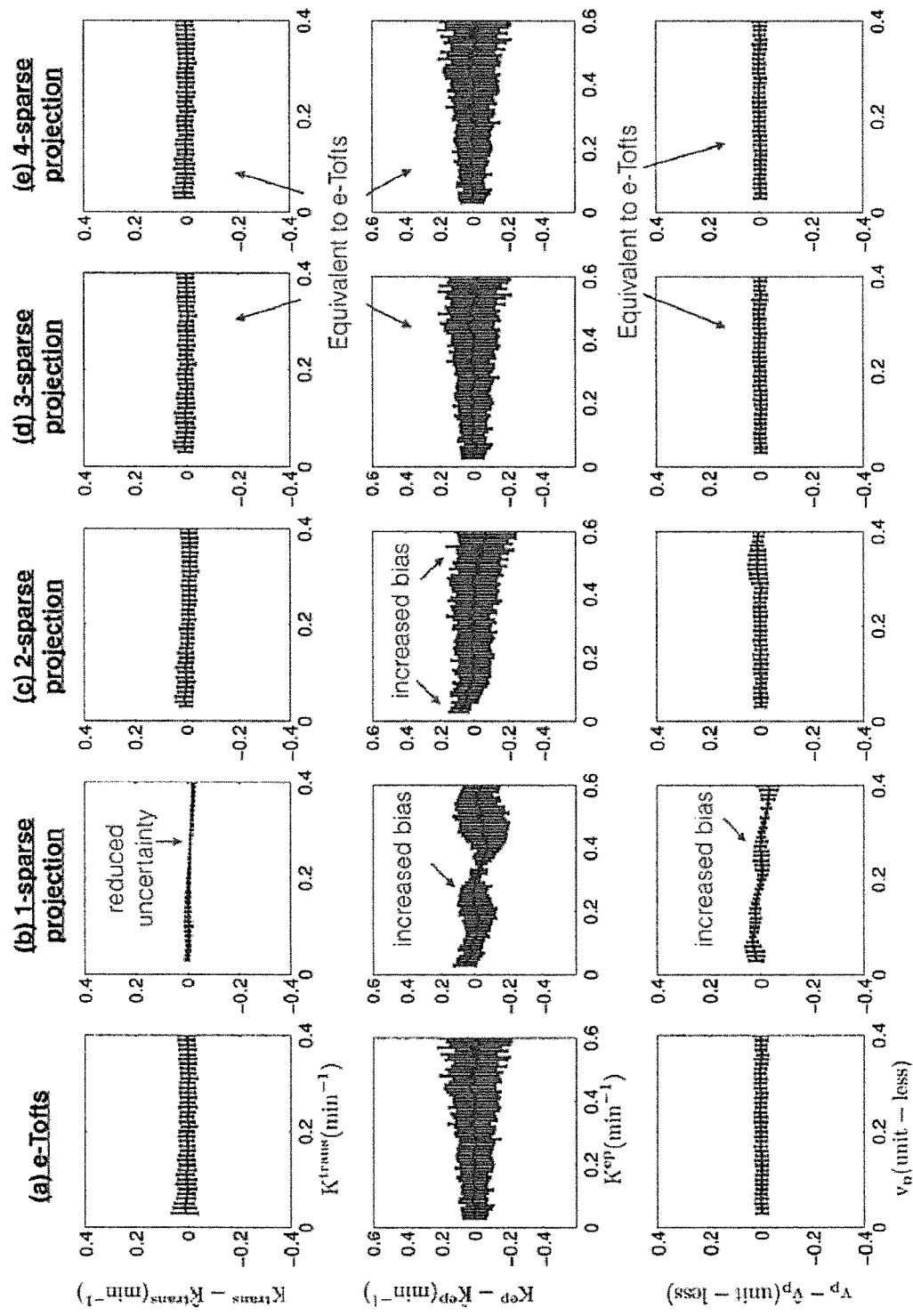
FIG. 3. Error statistics in estimating kinetic parameters using the e-Tofts model from the (a) noisy, (b-e) 1 to 4 sparse projected concentration time profiles. Estimating (top row) $K^{trans}$ with $v_p$=0.04, $K^{ep}$=0.2 min$^{-1}$, (middle row) $K^{ep}$ with $v_p$=0.2, $K^{trans}$=0.2 min$^{-1}$, (bottom row) $v_p$ with $K^{trans}$=0.2 min$^{-1}$, $K^{ep}$=0.4 min$^{-1}$.

Noise Sensitivity Analysis:

We analyzed the statistics of kinetic parameter estimation from 100 realizations of concentration profiles corrupted by white Gaussian noise (zero mean, standard deviation=0.001). In FIG. 3 from the chosen set of TK parameter ranges, note that as k is increased the error statistics in estimating the kinetic parameters from noisy data converge towards error statistics of kinetic parameter mapping with the e-Tofts model. For low values of k≤2, we observed bias, and reduced variance, and for high values of k>10 (not shown), we observe increased uncertainty. k=3 or 4 provided the best compromise, closely mimicking e-Tofts modeling.

Reconstruction:

The estimated concentration time profiles are estimated from fully sampled or under-sampled DCE-MRI measurements using minimization of an objective function that balances model-fitting and data consistency. In particular, the proposed method formulates the estimation of the concentration time profiles $C_{M \times N}$ (M-number of pixels; N-number of time frames) from the under-sampled k-t space data (b) as the following minimization problem:

$$\min_{X,U} \underbrace{\|C - UV\|_2^2}_{\text{model-fit error}}; \text{ s.t. } \underbrace{\|u_i\|_0 = k}_{\text{sparsity constraint}}; \underbrace{A(c) = b}_{\text{data-consistency}}; \qquad (2)$$

where A models Fourier under-sampling, coil-sensitivity encoding, and transformation between concentration and signal using knowledge of T1, M0, and flip angle maps obtained from calibration data; $U_{M \times r} V_{r \times N}$ denotes the k-sparse projection of C in the dictionary V. In this regard, inverse Fourier transform is the standard transformation to convert MRI raw data to image space and Forward Fourier transform (used here) is able to transform image into MRI raw data (k-space). Coil sensitivity maps are the weighting sensitivity of the image intensity for different MRI receiver coil, and are measured from the fully-sampled image beforehand. The transformation between concentration and signal is the spoiled echo gradient signal equation. "A" matrix represents all pre-known coefficient and transformation/model that are used in DCE-MRI. The above is solved by iterating between (a) updating U using orthogonal matching pursuit sparse projection (Pati, Y. C., Rezaiifar, R. and Krishnaprasad, P. S., 1993, November. Orthogonal matching pursuit: Recursive function approximation with applications to wavelet decomposition. In *Signals, Systems and Computers*, 1993. 1993 *Conference Record of The Twenty-Seventh Asilomar conference on* (pp. 40-44). IEEE; the entire disclosure of which is hereby incorporated by reference) and (b) enforcing consistency with acquired data. Starting with an initial guess of C obtained from view-sharing reconstruction, we iterate until a stopping criterion is achieved. An example of such a stopping criterion is $\|C_i - C_{i-1}\|_2 < e$. A value of e of about $10^{-6}$ is found to be sufficient. After the concentration-time profiles are obtained, kinetic parameters are estimated by fitting the profiles to a Toft or e-Tofts model.

Validation

We have performed retrospective under-sampling experiments on fully-sampled DCE-MRI data sets (3T, Cartesian T1 weighted spoiled gradient echo, FOV: 22×22×4.2 cm³ resolution: 0.9×1.3×7 mm³; 5 sec temporal resolution) from eight glioblastoma brain tumor patients with different tumor characteristics (shape, size, and heterogeneity). k-t under-sampling was performed using a randomized golden angle trajectory (see, Y. Zhu, Y. Guo, S. G. Lingala, R. Marc Lebel, M. Law, and K. S. Nayak, "GOCART: GOlden-angle CArtesian randomized time-resolved 3D MRI," *Magn. Reson. Imaging*, 2015; the entire disclosure of this is hereby incorporated by reference) at acceleration factors ranging from 5 fold to 30 fold. Image reconstruction was performed with both the proposed dictionary based approach, and compared with an existing compressed sensing approach that relies on temporal total variation sparsity. After image reconstruction, the ETK model was used to estimate the parameters Ktrans, Kep, Vp with a population based arterial input function. Performance was characterized quantitatively in terms of normalized mean square errors between the TK maps derived from the reconstructions and the fully-sampled images.

Figure 4:
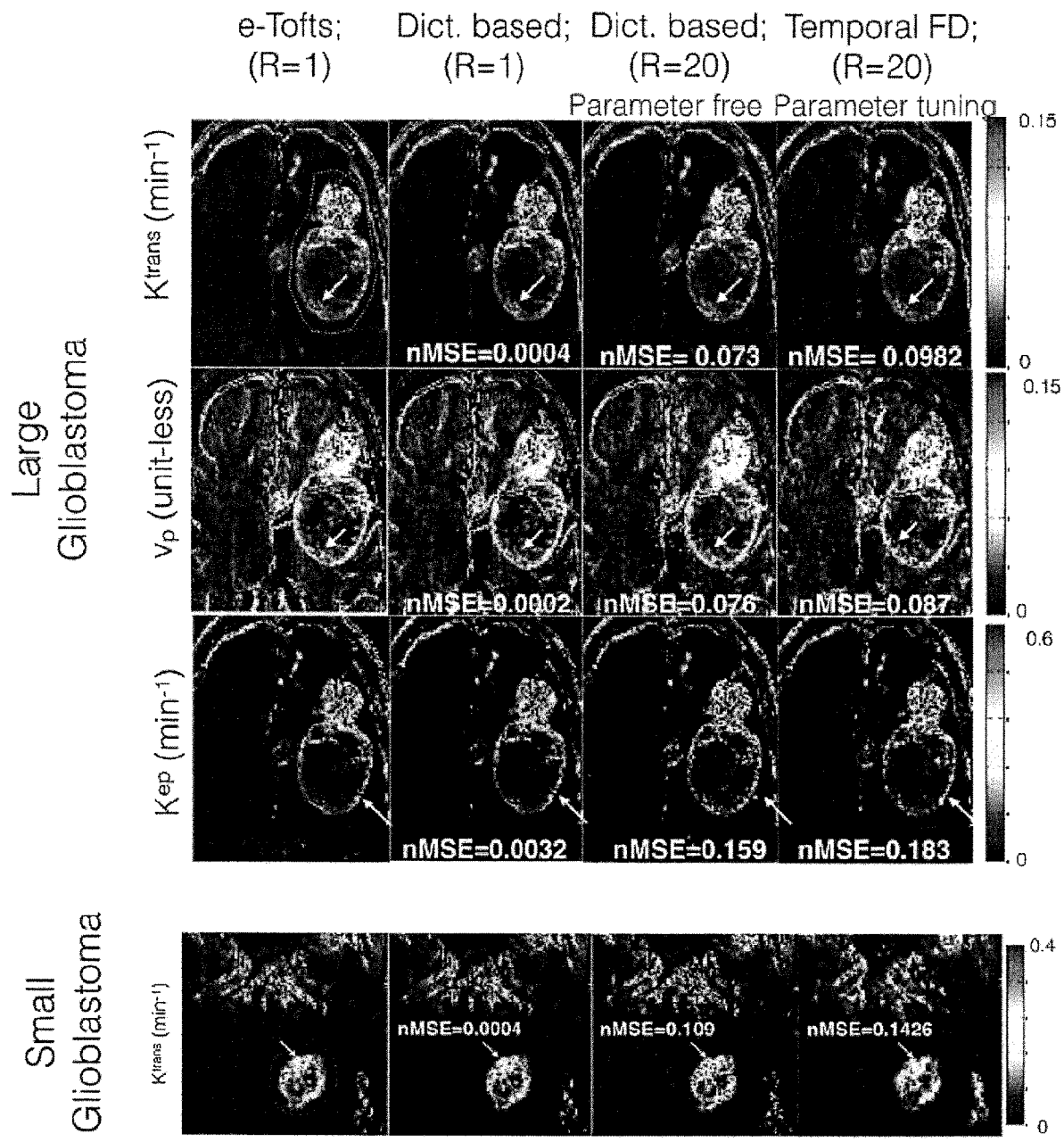
FIG. 4. Validation using retrospective under-sampling experiments. Shown here are comparisons using representative examples from a large glioblastoma and a small glioblastoma patient. The columns show parameter maps from (first) fully-sampled reference, (second) fully sampled with dictionary modeling, undersampled with a factor R=20 with (third column) dictionary modeling, and (fourth column) temporal finite difference reconstruction. Note the very low nMSE from the (×1) dictionary approach. At undersampling factor R=20, the nMSE is increased with the proposed approach, however the thin tumor margins are depicted with good fidelity in comparison with the temporal finite difference approach (see arrows). Also, note the proposed approach does not require tuning of any regularization parameters.

FIG. 4 shows comparisons on a case of large glioblastoma patient. The columns depicts the TK parameters derived respectively from fully-sampled data, the proposed dictionary based approach using fully sampled data, the proposed dictionary approach with under-sampled data at R=20, and temporal finite difference method at R=20. From the first two columns, it can be seen that the TK parameters derived after 3-sparse projection of the fully-sampled concentration time profiles onto the dictionary closely mimics those obtained from the fully-sampled data—which suggests equivalence of the 3-sparse projection with ETK modeling. At R=20, the TK parameters obtained from ETK modeling demonstrates robust depiction of the high spatial frequency information edges between the tumor core and the tumor boundaries, and also demonstrates improvements in normalized mean square errors compared with the temporal finite difference based reconstruction. Note, in contrast to dependence on tuning regularization parameter in the temporal finite difference scheme, the proposed dictionary based approach does not rely on tuning of any regularization parameters. Similar trends are observed in the small glioblastoma case shown in FIG. 4, where the proposed approach maintains sharp features in the reconstructed Ktrans maps, while the temporal finite difference approach depicted blurring of tumor boundaries.

Figure 5:
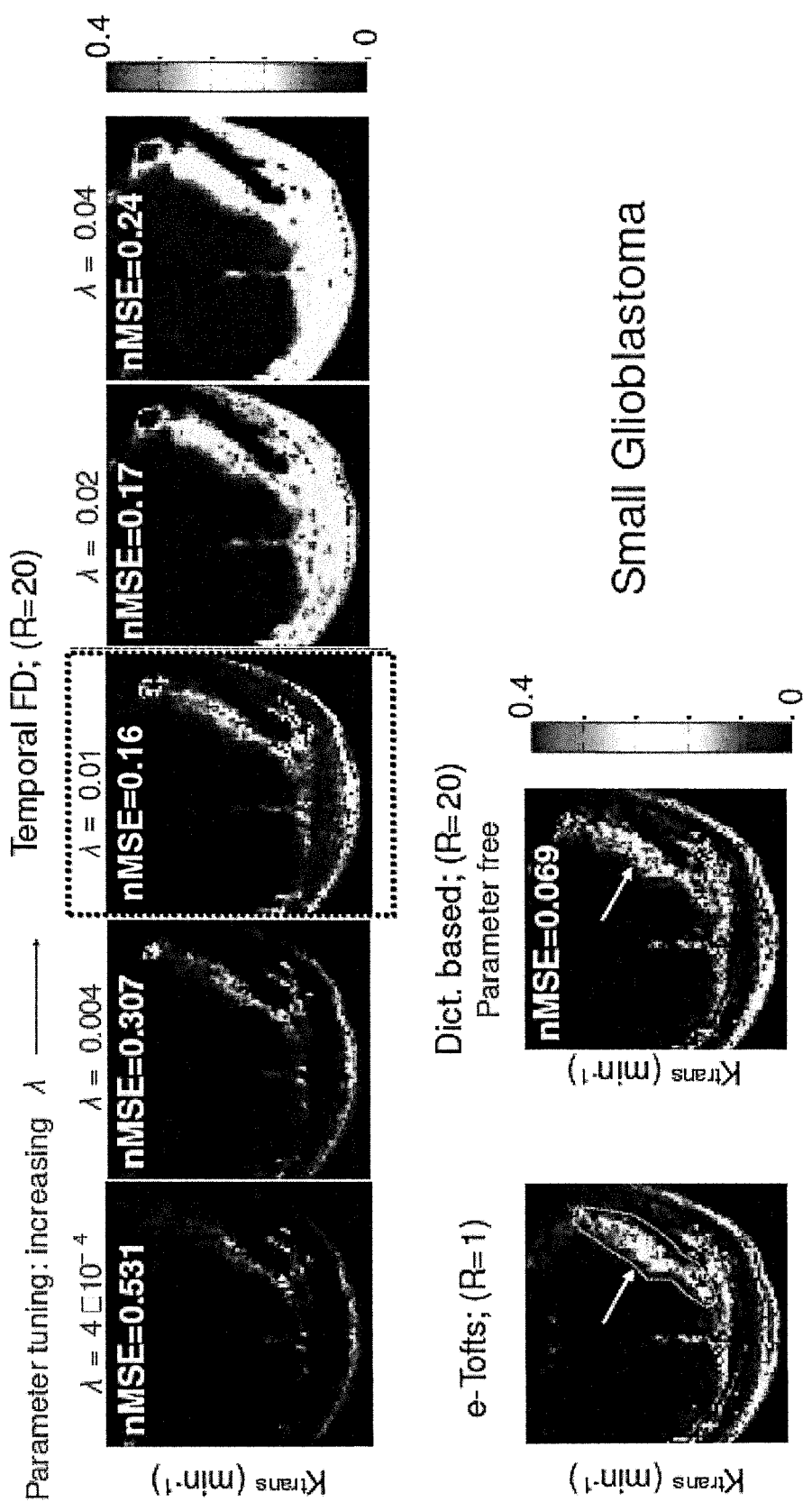
FIG. 5. Example demonstrating practical challenge in tuning regularization parameters in compressed sensing: Note the temporal finite difference approach relies on tuning a free parameter in the reconstruction, and produces varied estimates of the Ktrans map with different regularization parameters. In contrast, the proposed dictionary based approach provides a parameter free reconstruction and also provides robust estimation of TK parameters from undersampled data.

FIG. 5 demonstrates a representative example, which shows the practical challenge in tuning free regularization parameters associated with existing compressed sensing based approaches. In this retrospective downsampling experiment, since the ground truth fully sampled data was available, a strategy of tuning the free regularization parameter based on obtaining a minimal normalized mean square error between the reconstruction and the fully sampled data was adapted. Note that the estimates of the resultant Ktrans maps are highly variable with the adaption of different regularization parameters. The final estimated Ktrans based on the above strategy depicted severe under-estimation and also depicted blurring of the boundaries of the tumor. In contrast, the proposed dictionary approach produced robust depiction of Ktrans maps with lower errors compared to the compressed sensing approach (~2.3 fold lower). Furthermore, it does not rely on parameter tuning and implicitly imposes temporal constraints that utilize basis functions derived from the ETK model during the reconstruction.

Advantages Over Other Methods

DCE-MRI is not yet a clinical standard for evaluating tumor progress and treatment response. This is due to the limited coverage and poor resolution of traditional DCE-MRI techniques, and the high variability of different modeling and reconstruction methods. Traditional compressed sensing based methods tend to address the resolution and coverage problem via constrained reconstruction from under-sampled data. However, the performance is highly variable based on different constraints used and the tuning of regularization parameters. The proposed method is able to restore reliable TK parameters from under-sampled data at upto acceleration factors of 30 fold, without tuning any parameters. The knowledge of the TK model is used as temporal constraints in the reconstruction to better utilize the redundancy in full forward modeling pipeline of DCE-MRI, and therefore to obtain better quality parameter maps from under-sampled k-t measurements. The below session discusses advantages over existing approaches for under-sampled DCE-MRI reconstruction.

Flexibility to Handle any Tracer-Kinetic Model

The proposed framework is able to handle any TK model, including non-linear models by constructing an appropriate set of temporal basis functions from a chosen TK model. Utilizing the k-SVD dictionary learning algorithm, we have shown equivalence of any curve generated from the Patlak model can be synthesized by temporal dictionaries constructed with 2-sparse projection. Similarly, we have shown equivalence of the ETK model with dictionaries constructed with 3-sparse projection. The proposed framework therefore contrasts with existing direct reconstruction approaches, which are designed to efficiently handle linear models, but face challenges in convergence with non-linear models.

Improved Accuracy of TK Parameter Mapping at High Under-Sampling Factors

The proposed technique is able to achieve higher acceleration for the same data sets relative to a leading compressed sensing method. We performed the comparison in a total of eight fully-sampled data sets of brain tumor patients, and calculated the normalized Mean-Squared-Error (nMSE) of the TK parameter maps with respect to the maps from fully-sampled data. FIGS. 4 and 5 demonstrates two representative examples where the proposed method provides robust depictions of the TK maps at up to 20-fold. Consistent performance was observed in all the remaining cases.

Improved Ease of Use

As mentioned, we do not require tuning parameters for the proposed dictionary based reconstruction. The equivalence of the k-sparse projections with an appropriately chosen value of k to a particular TK model directly translates to fixing the choice of the sparsity parameter in the reconstruction, which would avoid tuning of any free parameters. The TK parameters are obtained by performing TK modeling on the reconstructed concentration time profiles from the proposed formulation. An example comparison highlighting the improved practical ease of use this method over an existing compressed sensing based temporal finite difference reconstruction method is highlighted in FIG. 5. In this context, the usage of the proposed approach is simple and straightforward for clinical applications.

Variations and Modifications

There are several variations and modifications of the proposed formulation to either improve it or generalize it to different applications. Listed below are all the possible adaptations that can be easily extended or incorporate into the proposed framework.

Alternate Ways of Constructing the Library and Dictionaries

A uniform grid of TK parameters was used to generate the library of possible concentration time profiles from a chosen TK model. It is possible to perform application-specific discretization of the TK parameters to improve sensitivity and accuracy in modeling time curves that lie in a particular zone in the TK parameter space. It is also possible to utilize different compression algorithms to construct temporal dictionaries from the library of all possible generated concentration time profiles from a chosen TK model. Variations include designing superior dictionary learning algorithms over k-SVD such as those which takes into account minimization of errors made in the TK parameter space as opposed to the errors made in the concentration v.s time profile space.

Formulation Modifications

It is possible to add additional constraints in the reconstruction formulation to improve well posednees and image quality at high under-sampling factors. Spatial wavelet, total variation, or other constraints on the image time series can be added as additional l1 or lp norms (p<1) to the optimization.

Alternate Trajectories

The adopted trajectory is Cartesian-based, and this can be easily adapted to other Cartesian-based under-sampling trajectories like Poisson-disc, TWIST, DISCO and so on. It is also easy to use non-Cartesian sampling pattern like spiral or radial, by adding the gridding step into the data consistency between images and raw data.

Adaption to Arterial Input Function Variations

The validation shown here is based on utilizing a population based Arterial Input Function (AIF). However, the framework is flexible to adapt to different AIFs by parameterizing the AIF shape into a handful of parameters such as dispersion, and delay parameters, and then constructing a richer library of profiles by varying the AIF parameters. The resultant learnt temporal dictionary will therefore take into account of changes in AIF shape specific to the patient.

Motion Compensation

It is flexible to add motion compensation as an additional constraint or directly in the data consistency term to improve consistency. The reconstruction formulation is no different than the data consistency term for current motion compensation techniques. Therefore, the motion can be estimated as motion field maps, and enforce these maps to correct the anatomic images during the reconstruction, or enforce them as additional constraints.

Other Body Parts

The flexibility to handle any TK model makes the proposed approach easily extendable to other body part like breast, liver or prostate, with the corresponding appropriate model for specific organ. The validation shown here is performed in brain tumor patients as an initial study, however, similar or same pulse sequence is used to acquire DCE-MRI images from other body parts, and therefore the proposed reconstruction can be applied to those body organs with the corresponding TK model.

Other Variations

The proposed dictionary based reconstruction framework can also be applied to other imaging applications that use a model to estimate certain parameters. For example it is applicable to dynamic susceptibility contrast based (DSC) perfusion imaging to estimate the blood flow and blood volume maps in various organs including brain, prostate, liver, or breast; and also in dynamic contrast enhanced computed tomography application where the imaging model would be changed during the formulation with the TK based dictionaries appropriately incorporated into the formulation.

Basic Requirements

A system for implementing the method for direct reconstruction of tracer-kinetic parameter maps in dynamic contrast enhanced magnetic resonance imaging is provided. With reference to FIG. 11, imaging system 10 includes magnetic resonance imaging system 14, which can be a fast low angle shot magnetic resonance imaging system. Magnetic resonance imaging system 14 includes coils 15 from which the (k, t) space data is collected. Typically, system 14 implements a standard SPGR imaging sequence with a modifiable sampling trajectory. In a refinement, only phase encoding directions need to be reordered. Imaging system 10 also includes a programmable computer system 16 for implementing the steps of applying compressing the library of simulated concentration time profiles to a dictionary of temporal basis functions; collecting magnetic resonance imaging data from an imaging volume or imaging plane in the subject over a predetermined period of time, the magnetic resonance imaging data including under-sampled k-t space data; and determining estimated concentration time profiles for the under-sampled k-t space data by finding estimated concentration time profiles that has an optimal projection of projection on the dictionary of temporal basis functions. Computer system 16 includes central processing unit (CPU) 18, memory 20, display 22 and input/output interface 24 which communicate over buses 26. Computer system 16 communicates input devices 30 such as a keyboard and mouse via input/output interface 24. In one variation, memory 20 includes one or more of the following: random access memory (RAM), read only memory (ROM), CDROM, DVD, disk drive, tape drive. The method of this variation is implemented by routine 32 that is stored in memory 20 and executed by the CPU 18. As set forth above, a Gadolinium-based or similar contrast agent for contrast injection is introduced into a subject for the imaging.

2. Method for Direct Reconstruction of Tracer-Kinetic Parameter Maps in Dynamic Contrast Enhanced Magnetic Resonance Imaging In another variation, a method for direct reconstruction of tracer-kinetic parameter maps in dynamic contrast enhanced magnetic resonance imaging is provided. The method includes steps of administering a magnetic resonance contrast agent to a subject and then collecting magnetic resonance imaging data from the subject. The magnetic resonance imaging data can include under-sampled (k,t)-space data. A tracer kinetic model is selected to be applied to the magnetic resonance imaging data. The tracer kinetic model is defined by a plurality of tracer kinetic parameters. Starting with an initial guess of tracer the kinetic parameters, the tracer kinetic model is applied to obtain contrast agent concentration versus time data. Dynamic anatomic images are obtained from the contrast agent concentration versus time data. Fourier transform, coil sensitivity and/or under-sampling patterning are applied to obtain propagated (k,t)-space data (i.e., estimated (k,t)-space data) from dynamic anatomic images. The (k,t)-space data from dynamic anatomic images is compared to measured (k,t)-space data. The tracker kinetic parameters are iteratively refined to minimize the errors between the measured and propagated (k,t)-space data.

The present variation provides a novel technique where the TK parameter maps are directly reconstructed from under-sampled raw MRI data. Because the TK model itself is enforced in the reconstruction, the temporal changes are better captured by this technique, and more accurate TK parameter maps can be restored event at very high under-sampling rates (up to 100×). Furthermore, the proposed method does not require tuning of any parameters, compared to constrained reconstruction where a number of regularization parameters need to be tuned. Direct reconstruction of parameter maps from raw data is popular in Positron Emission tomography (PET) imaging. Previous attempts of this technique to DCE-MRI have yielded very low under-sampling rates (around 4× to 8×), and it is achieved only in simulation data. Unlike previous methods, the proposed method considers the whole problem as an error minimization problem, and offers an efficient gradient-based algorithm to solve it. The resulting efficiency and performance is greatly improved.

Technical Description

Algorithm Overview

The main problem is to solve the TK parameter maps directly from acquired (and potentially under-sampled) MRI data. We formulate this as an optimization problem, where we minimize the $l_2$ errors between the acquired data and the forward modelling of the TK parameter maps. The reconstruction pipeline requires prior selection of a certain TK model, a fixed arterial-input-function (AIF) that is based on a population-averaged curve, and $T_1$ and $M_0$ maps which are typically acquired before the DCE scan. (see, G. J. M. Parker, C. Roberts, A. Macdonald, G. a Buonaccorsi, S. Cheung, D. L. Buckley, A. Jackson, Y. Watson, K. Davies, and G. C. Jayson, "Experimentally-derived functional form for a population-averaged high-temporal-resolution arterial input function for dynamic contrast-enhanced MRI.," Magn. Reson. Med., vol. 56, no. 5, pp. 993-1000, November 2006; the entire disclosure of which is hereby incorporated by reference).

Direct Reconstruction

Figure 6:
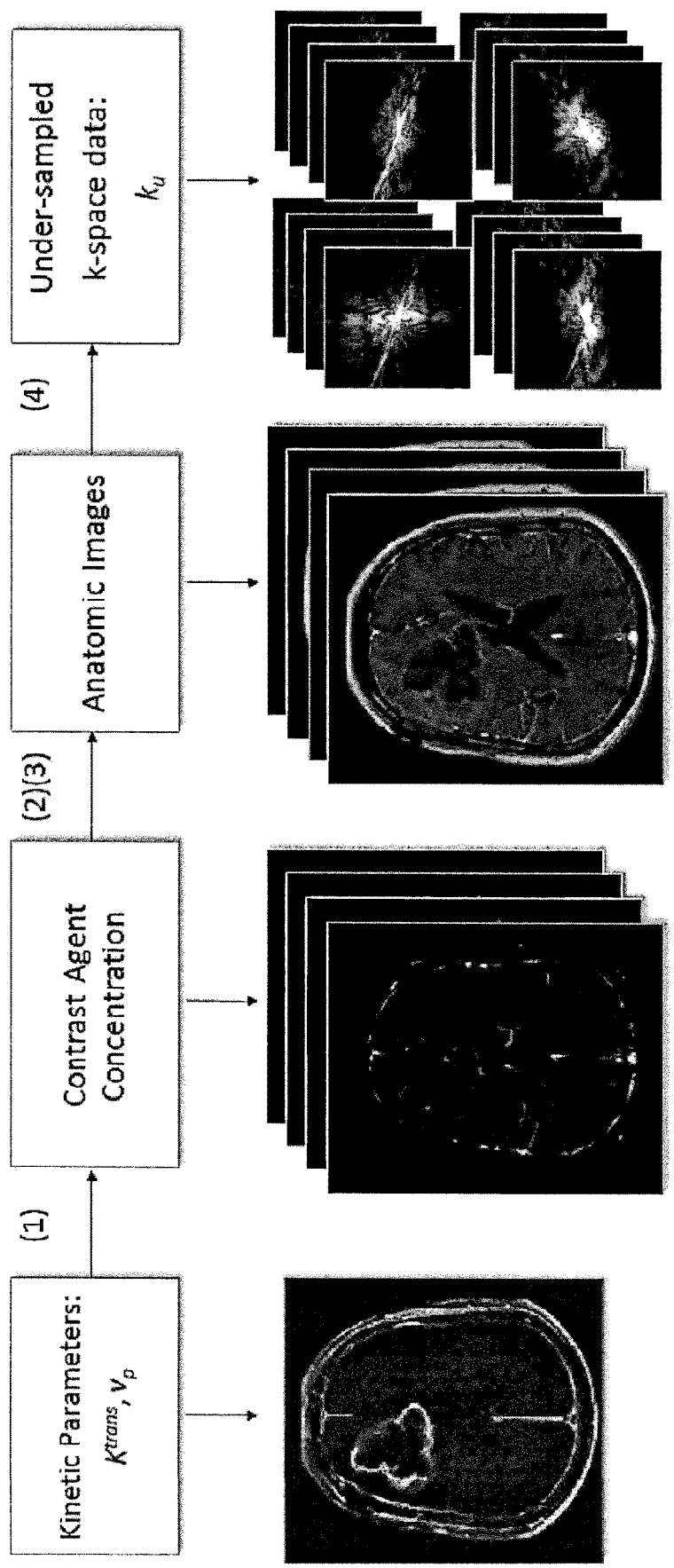
FIG. 6. Flowchart of the forward model.

The forward modelling from TK parameter maps to under-sampled k-space $k_u$ is illustrated in the flowchart in FIG. 6. The Patlak model is used to convert Tk parameter ($K^{trans}$, $v_p$) maps to contrast concentration over time, then the spoiled gradient echo signal equation is used to get the dynamic anatomic images. (P. S. Tofts, G. Brix, D. L. Buckley, J. L. Evelhoch, E. Henderson, M. V Knopp, H. B. Larsson, T. Y. Lee, N. a Mayr, G. J. Parker, R. E. Port, J. Taylor, and R. M. Weisskoff, "Estimating kinetic parameters from dynamic contrast-enhanced T(1)-weighted MRI of a diffusable tracer: standardized quantities and symbols," J. Magn. Reson. Imaging, vol. 10, no. 3, pp. 223-32, September 1999; the entire disclosure of which is hereby incorporated by reference). The Fourier transform, sensitivity maps and sampling pattern connect anatomic images to under-sampled k-space data. In this regard, inverse Fourier transform is the standard transformation to convert MRI raw data to image space and Forward Fourier transform (used here) is able to transform image into MRI raw data (k-space). Coil sensitivity maps are the weighting sensitivity of the image intensity for different MRI receiver coil, and are measured from the fully-sampled image beforehand. Sampling patterns are binary maps that record which point are sampled in the (k,t)-space (raw data space).

The flow chart indicates that we can use a general function $y(K^{trans}v_p)$ to denote the relationship between TK maps $K^{trans}$, $v_p$ and under-sampled (k,t)-space $k_u$.

$$k_u = y(K^{trans}, v_p)$$

We then solve for $K^{trans}$, $v_p$ as a least-square optimization problem. The reconstruction process (i.e., least-square optimization) is formulated as:

$$(K^{trans}(x, y, z), v_p(x, y, z)) = \mathrm{argmin}_{K^{trans}(x, y, z), v_p(x, y, z)} \|k_u - y(K^{trans}(x, y, z), v_p(x, y, z))\|_2^2$$

Tracer kinetic parameter maps are determined by an efficient gradient-based algorithm. An efficient gradient-based algorithm, limited-memory Broyden-Fletcher-Goldfarb-Shanno (l-BFGS) method, is used to solve the TK parameter maps directly from under-sampled data.

Validation

Imaging experiments for validation were performed on a GE signal Excite 3T scanner to reconstruct TK parameter maps directly from under-sampled raw data using proposed method.

In the retrospective study, fully-sampled data sets were acquired from brain tumor patients using 3D spoiled gradient echo (SPGR) sequence. The image parameters were: flip angle: 15°, TR/TE: 6/1.3 ms, FOV: 22×22×4.2 cm³, special resolution: 0.9×1.3×7.0 mm³, temporal resolution: 5s, 50 time frames. A Cartesian randomized golden-angle radial sampling (see, Y. Zhu, Y. Guo, R. M. Lebel, M. Law, and K. S. Nayak, "Randomized Golden Ratio Sampling For Highly Accelerated Dynamic Imaging," in ISMRM, 2014, p. 4365; and Y. Zhu, Y. Guo, S. G. Lingala, R. Mare Lebel, M. Law, and K. S. Nayak, "GOCART: GOlden-angle CArtesian randomized time-resolved 3D MRI," Magn. Reson. Imaging, 2015; the entire disclosure of these publications is hereby incorporated by reference) was used to retrospective under-sample the k-space data in kx-ky plane. In the prospective study, kx-ky plane Cartesian golden-angle radial sampling was used to continuously acquire data for 5 min with FOV: 22×22×20 cm³, spatial resolution: 0.9×0.9×1.9 mm³. pattern (see, S. Winkelmann, T. Schaeffter, T. Koehler, H. Eggers, and O. Doessel, "An optimal radial profile order based on the Golden Ratio for time-resolved MRI.," IEEE Trans. Med. Imaging, vol. 26, no. 1, pp. 68-76, January 2007; the entire disclosure of this is hereby incorporated by reference). Other parameters are the same as retrospective study. A net acceleration factor of 30× is used to achieve this high resolution and whole-brain coverage.

Figure 7:
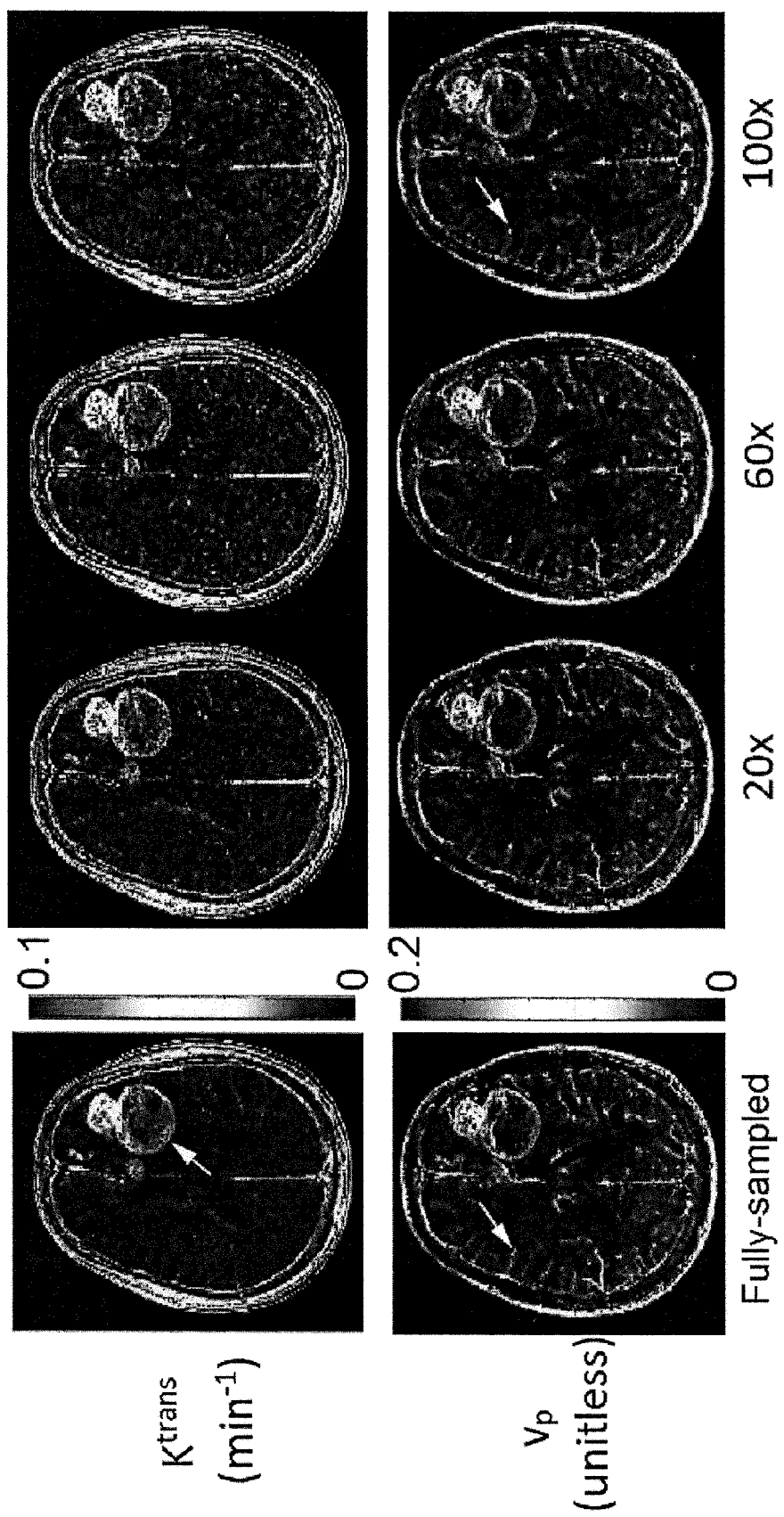
FIG. 7. Validation of proposed method in retrospective study.

FIG. 7 shows retrospective evaluation of direct reconstruction of $K^{trans}$ and $v_p$ maps. The proposed method is able to restore accurate TK parameter maps at high under-sampling rates up to 100×, with minimal degradation in image quality and clear delineation of tumor boundaries. Tiny vessel information on the $v_p$ maps are also preserved even at high under-sampling rates.

Figure 8:
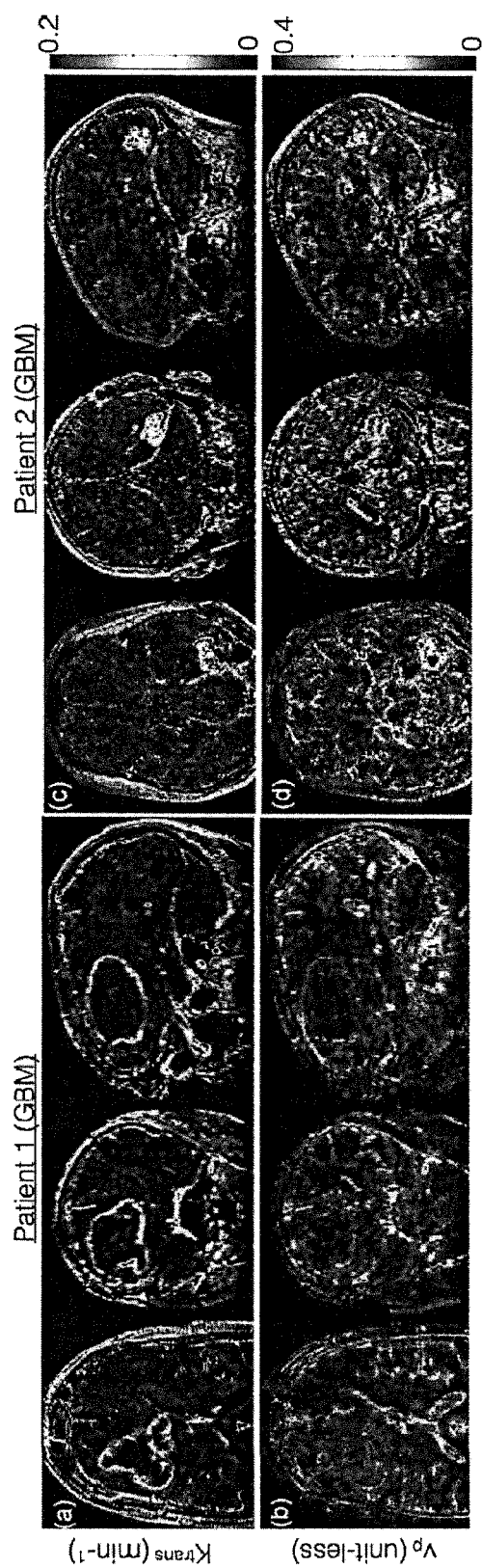
FIG. 8. Direct reconstruction results of $K^{trans}$ and $v_p$ maps from prospectively under-sampled data. Although lacking gold standard for the prospective studies, the direct reconstruction provides convincing TK parameter values for arbitrary reformatted planes, thus a complete pathological information is shown in a single scan.

FIG. 8 shows direct reconstruction results of $K^{trans}$ and $v_p$ maps from prospectively under-sampled data. Although lacking gold standard for the prospective studies, the direct reconstruction is able to provide convincing TK parameter values for arbitrary reformatted planes, thus a complete pathological information is shown in a single scan.

Advantages and Improvements Over Other Methods

DCE-MRI is not yet a clinical standard for evaluating tumor progress and treatment response. This is due to the limited coverage and poor resolution of traditional DCE-MRI techniques, and the high variability of different modeling and reconstruction methods. Traditional indirect methods tend to address the resolution and coverage problem via constrained reconstruction from under-sampled data. However, the performance is highly variable based on different constraints used and the turning of regularization parameters. The proposed method is able to restore accurate TK parameters from highly under-sampled data, without tuning any parameters. The full knowledge of the model us used in the reconstruction to better utilize the redundancy in DCE-MRI, and better quality parameter maps can be reconstructed directly from the raw data. The below session focusses on comparison to a state-of-the-art indirect method, where we reconstruct the anatomic images first using temporal sparsity constraint (finite difference), and derive the TK parameter maps from the reconstructed images. The indirect method is described in details in R. M. Lebel, J. Jones, J.-C. Ferre, M. Law, and K. S. Nayak, "Highly accelerated dynamic contrast enhanced imaging," Magn. Reson. Med., vol. 71, pp. 635-644, 2014; the entire disclosure of this is hereby incorporated by reference.

Improved Acceleration

Figure 9A:
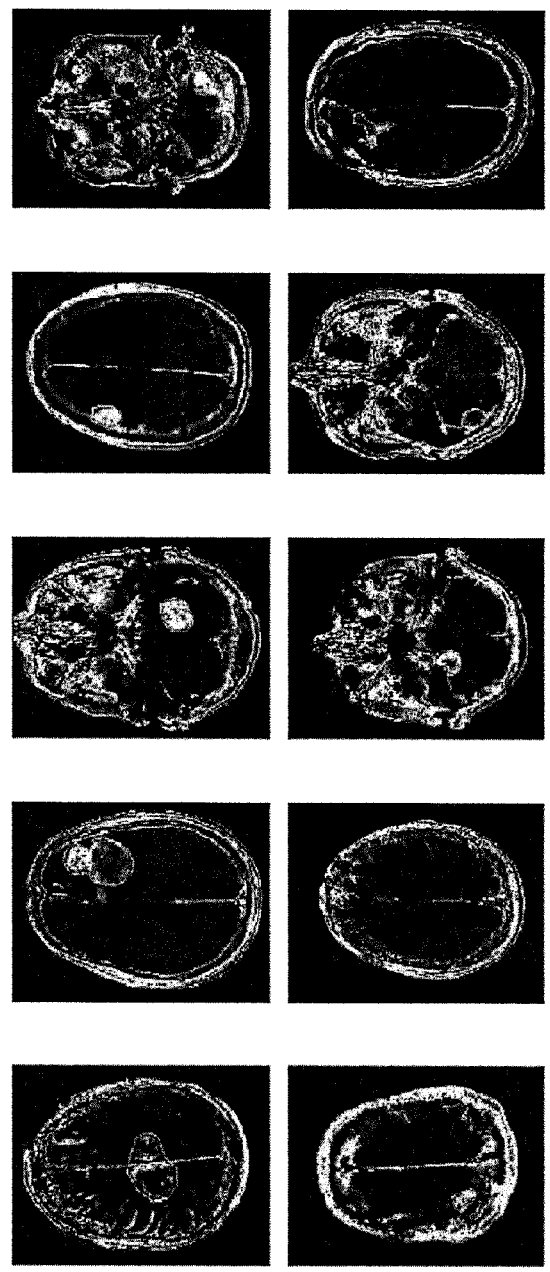
FIG. 9A. $K^{trans}$ and ROI selection for the 10 cases. Bottom: Comparison of rMSE performance in tumor ROI across under-sampling rates from 20× to 100×.
Figure 9B:
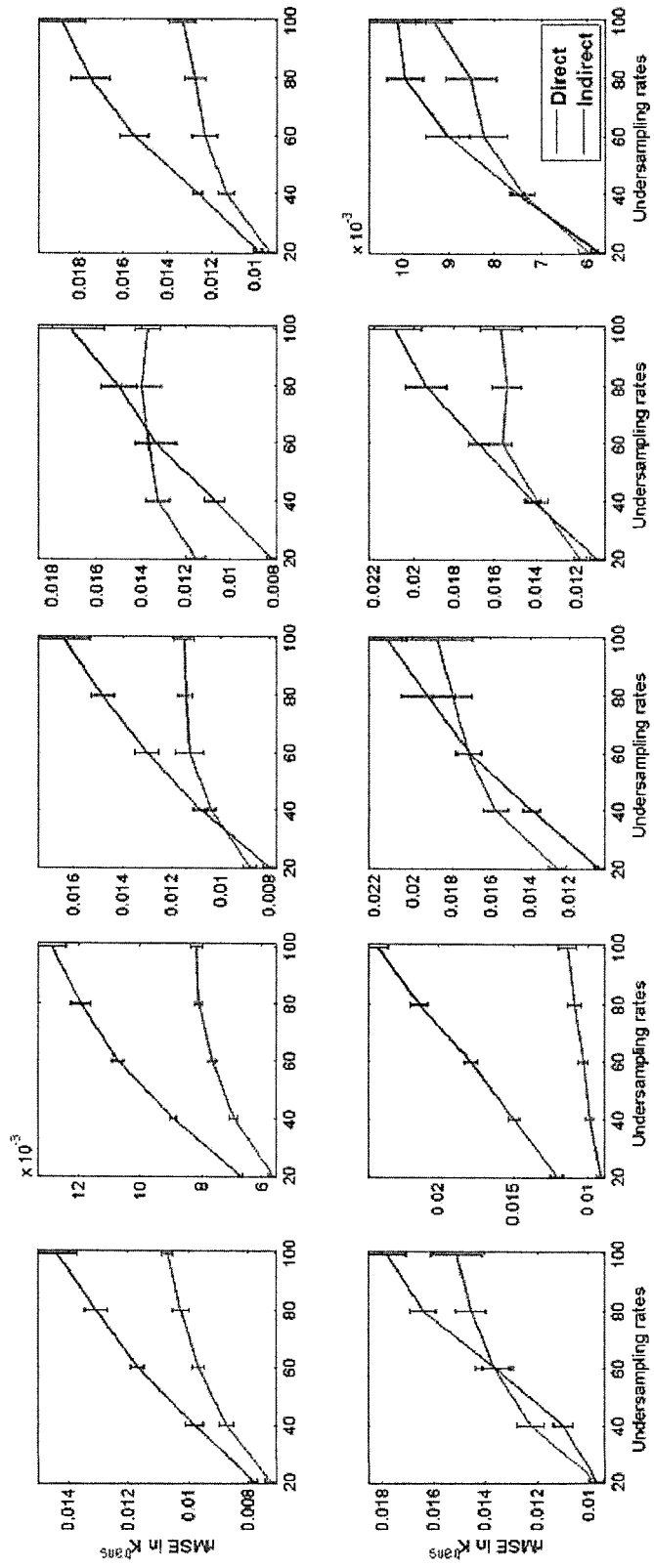
FIG. 9B. Lower rMSE values represent more accurate TK parameter values.

The proposed technique is able to achieve higher acceleration for the same data sets relative to a leading indirect method. We preformed the comparison in a number fully-sampled data sets of brain tumor patients, and calculated the root Mean-Squared-Error (rMSE) of the TK parameter maps with respect to the maps from fully-sampled data. FIG. 9 shows the rMSE performance of $K^{trans}$ in tumor ROI across under-sampling rates (20× to 100×) for 10 different data sets. The proposed method performed consistently better than the indirect method at high under-sampling rates for all cases.

Improved Accuracy

Figure 10:
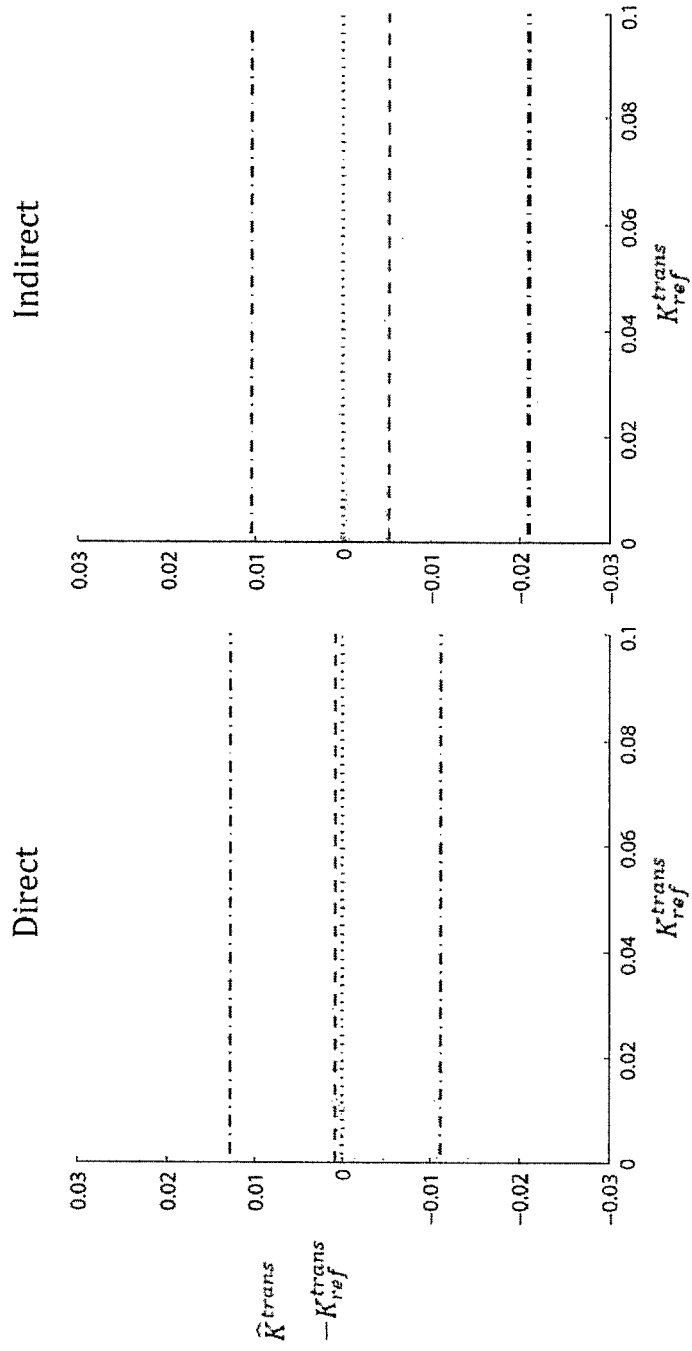
FIG. 10. Combined Bland-Altman plots of direct and indirect methods in tumor ROI at 60×.

The direct method provides more accurate values for the parameter maps. Bland-altman plots showing $K^{trans}$ data amalgamated from tumor ROIs in 13 subjects are shown in FIG. 10. Plots corresponding to direct and indirect estimation are shown for an acceleration rate of 60.

The indirect method has a substantial underestimation of $K^{trans}$, where the direct method has a smaller bias and variance. The indirect method also has an evident trend of setting 0 values for $K^{trans}$ values smaller than 0.02. This is possibly caused by the temporal finite difference constraints used in indirect method, where tiny changes of concentration may be mixed in high level of noise, and is smoothed out by the temporal constraint. Such trend is not observed in the direct reconstruction, showing that integrating the model is able to identify and restore those low-value of TK parameters.

Improved Robustness

For indirect methods, a greta effort has been made to ensure consistent and optimal performance by fine tuning the regularization parameters. And for TK parameter mapping in DCE-MRI, it is more difficult because the quality of the anatomic images does not guarantee the good quality of the TK parameter maps. However, all of these robustness issues are overcome by direct reconstruction, which has not free parameter.

Improved Ease of Use

As mentioned, we do not require tuning parameters for the direct reconstruction, and we do not need intermediate steps to output intermediate anatomic images. The TK parameters are directly output from the under-sampled data. Therefore the usage is simple and straightforward for clinical applications.

Variations and Modifications

The formulation of the direct reconstruction is similar to the data consistency term in other reconstruction algorithm, and thus different variations and improvements that exist for other methods can be easily adapted to the proposed method.

Algorithm Modifications

It is possible to add additional constraints to improve image quality. Spatial wavelet, total variation, or other constraints on the TK parameter maps can be added as additional $1_1$ norms to the optimization problem. Spatial wavelet constraint has been tested to improve the noise performance and convergence behavior of the proposed method.

For the optimization problem, other gradient-based algorithm like non-linear conjugate gradient (NLCG) can also be used to solve this minimization problem. NLCG algorithm has been tested and has shown slower convergence comparing to l-BFGS, but the resulting TK parameters are nearly identical.

Alternate Trajectories

The adopted trajectory is Cartesian-based, and this can be easily adapted to other Cartesian-based under-sampling trajectories like Poisson-disc, TWIST, DISCO and so on. It is also easy to use non-Cartesian sampling pattern like spiral or radial, by adding the gridding step into the data consistency between images and raw data.

Complex TK Models

The validation shown here is based on linear Patlak model. However, the direct reconstruction framework is extendable to other complete TK models like eTofts or 2 cxm models. Some preliminary results have shown that it is able to restore accurate TK parameter values for eTofts model, and the formulation is also flexible to be extended to other models as long as the gradient can be derived for a specific model.

Motion Compensation

It is flexible to add motion compensation as an additional constraint or directly in the data consistency term to improve consistency. The direct reconstruction formulation is no different than the data consistency term for current motion compensation techniques. Therefore, the motion can be estimated as motion field maps, and enforce these maps to correct the anatomic images during the reconstruction, or enforce them as additional constraints.

Joint Estimation

In the direct reconstruction framework, many values are predetermined (e.g. AIF, T1, M0, pre-contrast images). One or more of these values can be incorporated as unknowns in the optimization problem to be solved together with the TK parameters. This should result better fir for the data, but introduce larger variance and instability. For example, Fluckiger et al. introduce a parameterized AIF to be estimated together with TK parameters based on fully-sampled images. Similar method can also be applied in the direct reconstruction framework. (see, J. U. Fluckiger, M. C. Schabel, and E. V. R. DiBella, "Model-based blind estimation of kinetic parameters in dynamic contrast enhanced (DCE)-MRI," Magn. Reson. Med., vol. 62, no. 6, pp. 1477-1486, 2009; the entire disclosure of which is hereby incorporated by reference)

Complex Signal Based Contrast Concentration Conversion

In Simonis et al., it is proposed that the contrast concentration can be converted from complex-signal based image instead of magnitude image. (see, F. F. Simonis, A. Sbrizzi, E. Beld, J. J. Lagendijk, and C. A. van den Berg, "Improving the Arterial Input Function in Dynamic Contrast Enhanced Mill by fitting the signal in the complex plane," Magn. Reson. Med., vol. 00, no. 00, p. 00, 2015; the entire disclosure of which is hereby incorporated by reference). This improves the accuracy in AIF estimation. Similar technique can be applied in the direct reconstruction process since this conversion from contrast concentration to image signal exists in the reconstruction steps. The proposed method used traditional magnitude-based conversion, and this can be improved by this complex-signal based conversion for better TK parameter estimation.

Other Body Parts

It is extendable to other body part like breast, liver or prostate, with the corresponding appropriate model for specific organ. The validation shown here is performed in brain tumor patients as an initial study, however, similar or same pulse sequence is used to acquire DCE-MRI images from other body parts, and therefore the direct reconstruction can be applied to those body organs with the corresponding TK model.

Other Variations

The direct reconstruction framework can also be applied to other imaging applications that use a model to estimate certain parameters. For example it is applicable to dynamic susceptibility contrast based (DSC) perfusion imaging to estimate the blood flow and blood volume maps in various organs including brain, prostate, liver or breast.

Basic System Requirements

A system for implementing the method for direct reconstruction of tracer-kinetic parameter maps in dynamic contrast enhanced magnetic resonance imaging is provided. With reference to FIG. 11, imaging system 10 includes magnetic resonance imaging system 14, which can be a fast low angle shot magnetic resonance imaging system. Magnetic resonance imaging system 14 includes coils 15 from which the (k, t) space data is collected. Typically, system 14 implements a standard SPGR imaging sequence with a modifiable sampling trajectory. In a refinement, only phase encoding directions need to be reordered. Imaging system 10 also includes a programmable computer 16 for implement the steps of applying the tracer kinetic model to the magnetic resonance imaging data to obtain contrast agent concentration versus time data, extracting dynamic anatomic images from the contrast agent concentration versus time data, and connecting the dynamic anatomic images to the under-sampled (k,t)-space data. Computer system 16 includes central processing unit (CPU) 18, memory 20, displyer 22 and input/output interface 24 which communicate over buses 26. Computer system 16 communicates input devices 30 such as a keyboard and mouse via input/output interface 24. In one variation, memory 20 includes one or more of the following: random access memory (RAM), read only memory (ROM), CDROM, DVD, disk drive, tape drive. The method of the present variation is implemented by routine 32 that is stored in memory 20 and executed by the CPU 18. As set forth above, a Gadolinium-based or similar contrast agent for contrast injection is introduced into a subject for the imaging.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for improving dynamic contrast enhanced imaging, the method comprising:
   a) administering a magnetic resonance contrast agent to a subject;
   b) collecting magnetic resonance imaging data from the subject, the magnetic resonance imaging data including under-sampled (k,t)-space data from a plurality of receiver coils;
   c) selecting a tracer kinetic model to be applied to the magnetic resonance imaging data, the tracer kinetic model being defined by a plurality of tracer kinetic parameters;
   d) applying the tracer kinetic model to estimate tracer kinetic parameter maps;
   e) generating a library of simulated concentration time profiles for the magnetic resonance contrast agent by applying the tracer kinetic model;
   f) creating a compact dictionary of temporal basis functions from the library of simulated concentration time profiles; and
   g) determining estimated concentration time profiles for each spatial position from the under-sampled (k-t)-space data with an optimal projection onto the compact dictionary of temporal basis functions.

2. The method of claim 1 wherein step d) starts with an initial guess of the tracer kinetic parameter maps.

3. The method of claim 1 wherein the compact dictionary of temporal basis functions is formed by compressing the library of simulated concentration time profiles, using a dictionary learning algorithm.

4. The method of claim 3 wherein the dictionary learning algorithm is k-singular value decomposition (k-SVD).

5. The method of claim 1 wherein dictionary of temporal basis functions is a full library of simulated concentration time profiles.

6. The method of claim 1 wherein the tracer kinetic model is a Patlak model having kinetic parameters:
   $K^{trans}$ which is a transfer constant from blood plasma into extracellular extravascular space (EES); and
   $V_p$ which is a fractional plasma volume.

7. The method of claim 6 wherein the tracer kinetic model is an extended Tofts-Kety model further having kinetic parameter $K^{ep}$ which is a transfer constant from EES back to the blood plasma.

8. The method of claim 1 wherein the estimated concentration time profiles are modeled as a "k-sparse" linear combination of temporal basis functions in the compact dictionary of temporal basis functions such that a concentration time profile at each spatial position can be approximated using a linear combination of k temporal basis functions where k is a positive integer.

9. The method of claim 1 wherein the estimated concentration time profiles are estimated from fully sampled or under-sampled DCE-MRI measurements using minimization of an objective function that balances model-fitting and data consistency.

10. The method of claim 1 further comprising estimating kinetic parameters by fitting the estimated concentration time profiles to a Tofts model or an extended Tofts-Kety model having kinetic parameters:

$K^{trans}$ which is a transfer constant from blood plasma into extracellular extravascular space (EES); and $V_p$ which is a fractional plasma volume.

11. The method of claim 10 wherein the tracer kinetic model is the extended Tofts-Kety model further having kinetic parameter $K^{ep}$ which is a transfer constant from EES back to the blood plasma.

* * * * *